United States Patent
Cheng et al.

(10) Patent No.: US 10,398,697 B2
(45) Date of Patent: Sep. 3, 2019

(54) SOLID SOLUTION COMPRISING (6S)-5-METHYL TETRAHYDROFOLIC ACID OR SALT THEREOF, AND PREPARATION AND USE THEREOF

(71) Applicant: LIANYUNGANG JINKANG HEXIN PHARMACEUTICAL CO., LTD., Lianyungang, Jiangsu (CN)

(72) Inventors: Yongzhi Cheng, Lianyungang (CN); Zhi Cheng, Lianyungang (CN)

(73) Assignee: LIANYUNGANG JINKANG HEXIN PHARMACEUTICAL CO., LTD., Lianyungang (CN)

( * ) Notice: Subject to any disclaimer, the term of this patent is extended or adjusted under 35 U.S.C. 154(b) by 5 days.

(21) Appl. No.: 15/509,014

(22) PCT Filed: Sep. 4, 2015

(86) PCT No.: PCT/CN2015/088925
§ 371 (c)(1),
(2) Date: Mar. 6, 2017

(87) PCT Pub. No.: WO2016/034145
PCT Pub. Date: Mar. 10, 2016

(65) Prior Publication Data
US 2017/0273984 A1 Sep. 28, 2017

(30) Foreign Application Priority Data
Sep. 4, 2014 (CN) .......................... 2014 1 0449916

(51) Int. Cl.
| | |
|---|---|
| A61K 9/08 | (2006.01) |
| A61K 31/519 | (2006.01) |
| A61K 47/22 | (2006.01) |
| C07D 475/04 | (2006.01) |

(52) U.S. Cl.
CPC ............ *A61K 31/519* (2013.01); *A61K 47/22* (2013.01); *C07D 475/04* (2013.01); *A61K 9/08* (2013.01)

(58) Field of Classification Search
None
See application file for complete search history.

(56) References Cited

U.S. PATENT DOCUMENTS 6,441,168 B1   8/2002 Muller et al.

FOREIGN PATENT DOCUMENTS

| CN | 102612358 A | 7/2012 |
|---|---|---|
| CN | 102702200 A | 10/2012 |
| CN | 102775408 A | 11/2012 |
| CN | 102813656 A | 12/2012 |
| CN | 103450202 A | 12/2013 |
| CN | 103694239 A | 4/2014 |
| WO | 2009/103334 A1 | 8/2009 |
| WO | 2013/107236 A1 | 7/2013 |
| WO | 2013/163917 A1 | 11/2013 |

OTHER PUBLICATIONS

Liu, Y., et al. J. Food Sci. (2012), 77(2); pp. C236-C243 (Year: 2012).*
Saffoon, J., et al. JAPS (2011), 1(7); pp. 13-20 (Year: 2011).*
K. Ratanas Thien et al., "Serum folates in man," J. Clin. Pathol., The Department of Chemistry, University of Aston in Birmingham, vol. 30, pp. 438-448, 1977.
John A. Blair et al., "Autoxidation of 5-Methyl-5,6,7,8-tetrahydrofolic Acid", Department of Chemistry, University of Aston in Birmingham, pp. 18-21, 1975.
"Opinion of the Scientific Panel on Food Additives, Flavourings, Processing Aids and Materials in Contact with Food on a request from the Commission related to Calcium L-Methylfolate", The EFSA Journal, vol. 135, pp. 1-20, 2004.
Nov. 24, 2015 International Search Report issued in International Patent Application No. PCT/CN2015/088925.
Nov. 24, 2015 Written Opinion issued in International Patent Application No. PCT/CN2015/088925.

* cited by examiner

*Primary Examiner* — Kevin S Orwig
(74) *Attorney, Agent, or Firm* — Oliff PLC

(57) ABSTRACT

Disclosed are a composition including (6S)-5-methyl tetrahydrofolic acid or a salt thereof, and preparation and use thereof. In the composition, the content of (6S)-5-methyl tetrahydrofolic acid or the salt thereof is not less than 98.0%, the content of a related impurity JK12A is not greater than 0.1%, and 5-methyl tetrahydropterioic acid is not detectable.

13 Claims, 1 Drawing Sheet

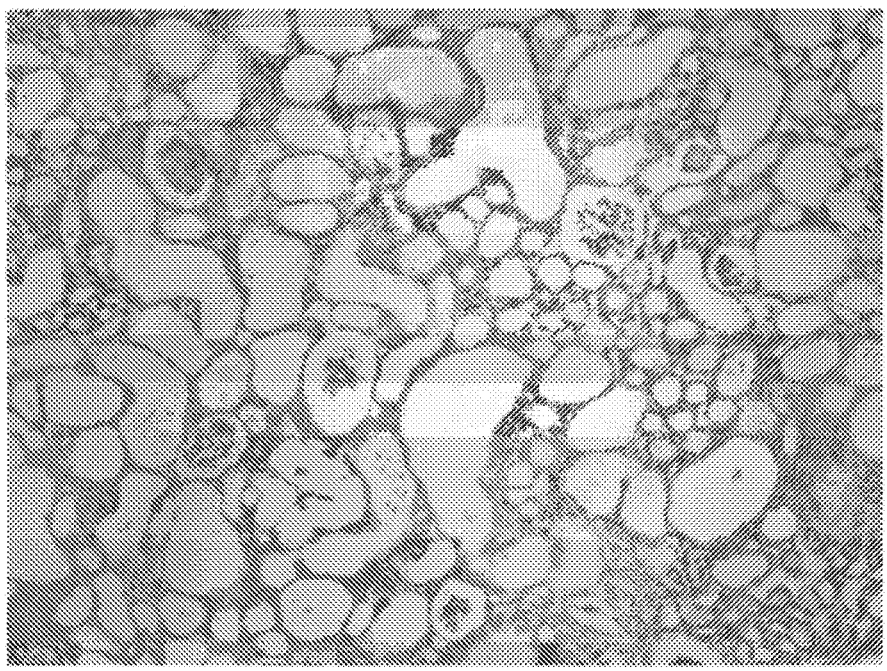

SOLID SOLUTION COMPRISING (6S)-5-METHYL TETRAHYDROFOLIC ACID OR SALT THEREOF, AND PREPARATION AND USE THEREOF

BACKGROUND

Technical Field

The present invention relates to the technical field of pharmaceutical preparations, and particularly to a composition comprising (6S)-5-methyl tetrahydrofolic acid or a salt thereof, a preparation method therefor, a solid solution composition comprising high-purity (6S)-5-methyl tetrahydrofolic acid or a salt thereof, a preparation method therefor, and use of (6S)-5-methyl tetrahydrofolic acid and salts thereof, including the use of the composition or the solid solution comprising (6S)-5-methyl tetrahydrofolic acid or a salt thereof, in which a pharmaceutically acceptable reductive substance is added as a stabilizing agent. The safe method of using provides excellent safety properties of (6S)-5-methyl tetrahydrodrofolic acid products.

Related Art

In recent years, more and more research is conducted on the physiological activity for human of 5-methyl tetrahydrofolic acid and salts thereof. Good application prospects are exhibited when 5-methyl tetrahydrofolic acid or a salt thereof is used as a folic acid supplement to human for preventing and/or treating neurological disorders; used in combination with 5-fluorouracil or methotrexate for tumor therapy; used in the treatment of pathophysiology of vascular and cardiovascular diseases; and used in the therapy and adjuvant therapy of severe depression and severe senile dementia.

However, 5-methyl tetrahydrofolic acid or a salt thereof is quite labile, very susceptible to degradation, and highly sensitive particularly to oxygen and moisture. Therefore, a composition comprising 5-methyltetrahydrofolate or a salt thereof, such as a pharmaceutical preparation, generally suffers from the problems of poor stability, easy discoloration, darkened color, remarkably lowered content, and increased degradation product.

Many papers concern the oxidative degradation of 5-methyl tetrahydrofolic acid or its single active isomer (6S)-5-methyl tetrahydrofolic acid. Unfortunately, according to a study by the present inventors, many previous discussions on the primary oxidation products of 5-methyl tetrahydrofolic acid are either unilateral or even erroneous. These conclusions mislead people to reduce the quality requirements for 5-methyl tetrahydrofolic acid. Based on the discussions in Ratanasthien K et al. Serum folates in man (Ratanasthien K., Blair J. A., Leeming R. J., Cooke W. T. and Melikian V. (1977). J. Clin. Path. 30: 438-448); Blair J. A et al. Autoxidation of 5-Methyl-5,6,7,8-tetrahydrofolic acid (Blair J. A., Pearson A. J. and Robb A. J. (1975). J. C. S. Perkin II, p. 18-21.); and European Food Safety Authority, Opinion of the Scientific Panel on Food Additives, Flavourings, Processing Aids and Materials in Contact with Food on a request from the Commission related to Calcium L-Methylfolate Question (The EFSA Journal (2004) 135. 1-20), 5-methyl tetrahydrofolic acid is initially oxidized into 5-methyl dihydrofolic acid in the presence of an oxidant.

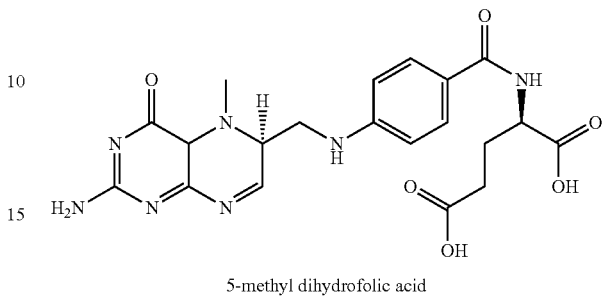

5-methyl dihydrofolic acid

In other literatures, the primary oxidation product is characterized as 4-hydroxy-5-methyl tetrahydrofolic acid. This product is inferred to be not toxic according to the structure.

An efficient method is developed by the present inventors, in which a high-purity primary oxidation product of 5-methyl tetrahydrofolic acid is prepared firstly. A series of studies are conducted (PCT/CN2013/073959) and it is found unexpectedly that the primary oxidation product of 5-methyl tetrahydrofolic acid or a salt thereof is JK12A having a structural formula of

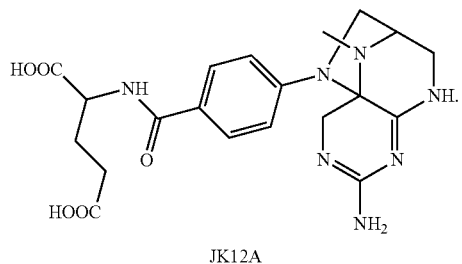

JK12A

JK12A is a primary oxidation product of 5-methyl tetrahydrofolic acid, which, depending on specific conditions, has a relative retention time from the main peak of about 0.36 under the detection conditions of the present invention, and is also known as 5-methyl-dihydrofolic acid or 4-hydroxy-5-methyl-tetrahydrofolic acid in relevant literatures.

It is a product of new structure, and this finding overturns the previous conclusions, including those in the above-mentioned literatures. In general, large changes in structure will lead to a significant change in physiological activity. Subsequent studies show that JK12A has a significant inhibitory effect on T lymphocyte proliferation. It is generally believed that this causes the reduction of human immunity.

| Control | Concentration determined M | Mean OD | SD | Cell survival rate | Cell control Stimulus control | T lymphocyte Stimulus with Con A Mean CPM 43977 | SD 8000 | T cell proliferation Comprehensive evaluation Percent enhancement/ inhibition |
|---|---|---|---|---|---|---|---|---|
| | | 0.122 | 0.003 | | | | | |
| JK12A | 100.000 | 0.089 | 0.002 | 73% | | | | |
| | 40.000 | 0.109 | 0.006 | 89% | | 43537 | 4110 | −1% |

| Control | Concentration determined M | Mean OD 0.122 | SD 0.003 | Cell survival rate | Cell control Stimulus control | T lymphocyte Stimulus with Con A Mean CPM 43977 | SD 8000 | T cell proliferation Comprehensive evaluation Percent enhancement/ inhibition |
|---|---|---|---|---|---|---|---|---|
| | 16.0 | 0.113 | 0.007 | 92% | | 36061 | 241 | −18% |
| | 6.4 | 0.103 | 0.007 | 84% | | 30784 | 3903 | −30% |
| | 2.56 | 0.076 | 0.008 | 62% | | 25507 | 10004 | −42% |
| | 1.024 | 0.073 | 0.014 | 59% | | 17590 | 8005 | −60% |
| | 0.41 | 0.052 | 0.015 | 75% | | 14073 | 10299 | −68% |
| | 0.164 | | | | | 40459 | 7501 | −8% |

An acute toxicity study of JK12A shows that at a dose of 2000 mg/kg, the test mice are killed on the spot within 1 minute. However, the anatomical findings show no significant changes in both the liver and the kidney, suggesting that the compound may possibly toxically target other tissues or organs and has a significant acute toxicity.

The present inventors find through studies that 5-methyl tetrahydropterioic acid is another common impurity in the product 5-methy tetrahydrofolic acid. Similar to the formation of JK12A, the impurity is oxidized to form JK1303 having a structure below

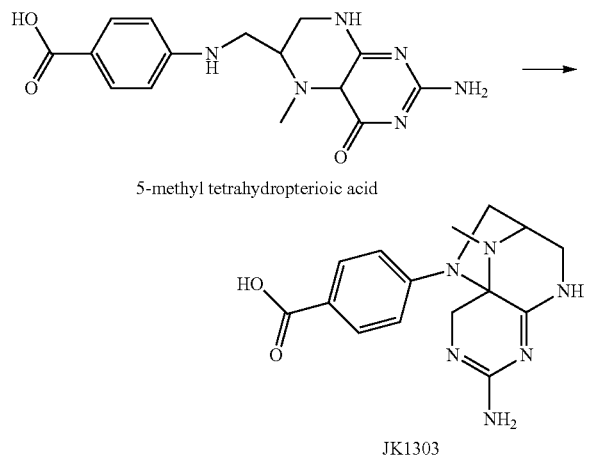

5-methyl tetrahydropterioic acid

JK1303

Subsequent studies have found that JK1303 has serious renal toxicity. 14 days after the mice are given a single dose of JK1303 at a dosage of 1000 mg/kg, severe renal tubular necrosis of the mice occurs, and a large number of vacuoles are anatomically found in the renal tubules. The toxicity of the primary oxidation product of 5-methyl tetrahydropterioic acid is also significantly changed.

The above experiments show that in a product containing 5-methyl tetrahydrofolic acid and its salt, the impurity JK12A produced from the oxidative degradation of 5-methyl tetrahydrofolic acid and its salt, and the oxidation product JK1303 of 5-methyl tetrahydropterioic acid are very harmful to human body, and this cannot and should not be ignored. Therefore, it is necessary to develop a solution for using 5-methyl tetrahydrofolic acid or its salt safely and reliably.

Chinese Patent No. CN102612358 discloses particles of stabilized salt of 5-methyl tetrahydrofolic acid, in which a crystalline salt of 5-methyl tetrahydrofolic acid is embedded in a wax to increase the stability.

Chinese Patent No. CN102813656 discloses a composition comprising stabilized salt of 5-methyl tetrahydrofolic acid, in which one or more amino acids free of mercapto groups are contained to increase the stability.

U.S. Pat. No. 6,441,168 discloses that the stability of 5-methyl tetrahydrofolic acid calcium salt is considerably increased by preparing it into a crystal form. However, the crystal form has a large particle size, is dissolved slowly, and needs to be ground first during the production of preparations, which trends to increase the risk of oxidation of 5-methyl tetrahydrofolic acid.

Chinese Patent No. CN2012086794 discloses a new crystal form of (6S)-5-methyl tetrahydrofolic acid calcium salt, which has good chemical stability and greatly increased solubility, such that no grinding is needed during the production of preparations. However, the content of the impurities such as JK12A is still high, and trends to increase gradually with the elapse of time.

It is also reported in literatures that 5-methyl tetrahydrofolic acid is embedded in microcapsules prepared with cellulose, shellac and other materials, to improve the stability of the active ingredients 5-methyl tetrahydrofolic acid in the preparation product.

However, the content of JK12A still cannot be controlled at a level that is safe enough by all these measures. For the raw medicine products of 5-methyl tetrahydrofolic acid commercially available at present, the total content of the impurities in a crystal form of 5-methyl tetrahydrofolic acid is generally in the range of 1-4%, in which the content of JK12A is up to 0.3-3.0%. In commercially available amorphous products, the total content of the impurities is as high as 10% or above, causing a serious threat to the safety of drugs during use. These facts show that the impurities including JK12A contained in all of these raw medicine products are not properly treated at present. The high chemical lability also makes it difficult to precisely control the dosage during use. For example, at a common dose of 0.451 mg, lability brings about a large deviation to the actual dose.

SUMMARY

In view of the prior art, an objective of the present invention is to provide a composition comprising high-purity (6S)-5-methyl tetrahydrofolic acid or a salt thereof, and a preparation method therefor.

Another objective of the present invention is to provide a solid solution comprising (6S)-5-methyl tetrahydrofolic acid or a salt thereof and a stabilizing agent, and a preparation method therefor.

A third objective of the present invention is to provide a pharmaceutical composition comprising high-purity (6S)-5-methyl tetrahydrofolic acid or a salt thereof, or the solid solution.

A fourth objective of the present invention is to provide use of the high-purity (6S)-5-methyl tetrahydrofolic acid or a salt thereof, or the solid solution comprising (6S)-5-methyl tetrahydrofolic acid or a salt thereof and a stabilizing agent, in medical areas.

The objectives of the present invention can be accomplished through the following.

A composition comprising (6S)-5-methyl tetrahydrofolic acid or a salt thereof is provided, in which the content of (6S)-5-methyl tetrahydrofolic acid or the salt thereof is not less than 98.0%, the content of a related impurity JK12A is not greater than 0.1%, and 5-methyl tetrahydropterioic acid is not detectable.

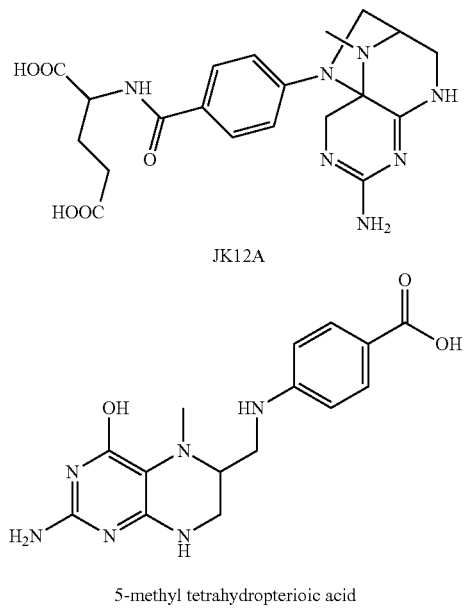

The composition comprising (6S)-5-methyl tetrahydrofolic acid or a salt thereof according to the present invention is composed essentially of (6S)-5-methyl tetrahydrofolic acid or a salt thereof. The content of (6S)-5-methyl tetrahydrofolic acid or the salt thereof in the composition is a content in percentages by weight of (6S)-5-methyl tetrahydrofolic acid or the salt thereof, or a content as detected by HPLC, and generally a content in weight.

In an embodiment, the content of (6S)-5-methyl tetrahydrofolic acid or the salt thereof in the composition is not less than 99.0%, the content of the related impurity JK12A is not greater than 0.1%, and 5-methyl tetrahydropterioic acid is not detectable.

In another embodiment, the content of (6S)-5-methyl tetrahydrofolic acid or the salt thereof in the composition is not less than 99.5%, the content of the related impurity JK12A is not greater than 0.1%, and 5-methyl tetrahydropterioic acid is not detectable.

In another embodiment, the content of (6S)-5-methyl tetrahydrofolic acid or the salt thereof in the composition is not less than 99.8%, the content of the related impurity JK12A is not greater than 0.05%, and 5-methyl tetrahydropterioic acid is not detectable.

The salt of (6S)-5-methyl tetrahydrofolic acid in the present invention is selected from a potassium salt, a sodium salt, a calcium salt, a magnesium salt, a barium salt, a zinc salt, a D-glucosamine salt, a D-galactosamine salt, or an arginine salt, and preferably a calcium salt, a D-glucosamine salt, a D-galactosamine salt or an arginine salt.

A method for preparing the composition comprising (6S)-5-methyl tetrahydrofolic acid or a salt thereof is provided. The method includes a method A or a method B.

The method A includes reacting a crude salt of (6S)-5-methyl tetrahydrofolic acid with a reverse reducing agent in water at pH 6-8 at a temperature of 50-90° C. directly, or reacting ultrasonically, to obtain a composition comprising a salt of (6S)-5-methyl tetrahydrofolic acid after reaction;

The method B includes reacting crude (6S)-5-methyl tetrahydrofolic acid, a reverse reducing agent, and a corresponding salt in water at pH 6-8 at a temperature of 50-90° C., or reacting ultrasonically, to obtain a composition comprising a salt of (6S)-5-methyl tetrahydrofolic acid after reaction In the method A or B, the reverse reducing agent is one or more selected from vitamin C, an ester of vitamin C, a salt of vitamin C, isovitamin C, an ester of isovitamin C, a salt of isovitamin C, mercaptoethanol, cysteine, mercaptoethane sulfonic acid, dithiothreitol, reductive glutathione, or zinc sulfate.

In a preferred embodiment, the reverse reducing agent in the method A or B is one or more selected from vitamin C, an ester of vitamin C, a salt of vitamin C, isovitamin C, an ester of isovitamin C, or a salt of isovitamin C, and preferably one or more of vitamin C, a sodium salt of vitamin C, a potassium salt of vitamin C, a calcium salt of vitamin C, a magnesium salt of vitamin C phosphate, a sodium salt of vitamin C phosphate, or isovitamin C, and most preferably vitamin C or isovitamin C; and the corresponding salt is a chloride, and preferably calcium chloride, magnesium chloride, and zinc chloride.

In a preferred embodiment, during the reaction of the method A or B, the reaction temperature is 60-80° C., and the pH is 7-7.5 and adjusted preferably with sodium hydroxide; and the concentration of the reverse reducing agent in water is not less than 2%, preferably not less than 20%, and further preferably not less than 40%, by weight.

A solid solution comprising (6S)-5-methyl tetrahydrofolic acid or a salt thereof and a stabilizing agent is provided, where the solid solution is composed essentially of (6S)-5-methyl tetrahydrofolic acid or a salt thereof and the stabilizing agent. The total content of the stabilizing agent and (6S)-5-methyl tetrahydrofolic acid or the salt thereof in a liquid chromatogram of the solid solution is greater than 99.5%. The stabilizing agent is one or more selected from vitamin C, an ester of vitamin C, a salt of vitamin C, isovitamin C, an ester of isovitamin C, a salt of isovitamin C, dithiothreitol, reductive glutathione, or zinc sulfate.

In a preferred embodiment, the total content of the stabilizing agent and (6S)-5-methyl tetrahydrofolic acid or the salt thereof in a liquid chromatogram of the solid solution comprising (6S)-5-methyl tetrahydrofolic acid or the salt thereof and the stabilizing agent is greater than 99.8%, and preferably greater than 99.9%. The (6S)-5-methyl tetrahydrofolic acid or the salt thereof is the high-purity (6S)-5-methyl tetrahydrofolic acid or a salt thereof according to claim 1.

In a preferred embodiment, the stabilizing agent is one or more selected from vitamin C, an ester of vitamin C, a salt of vitamin C, isovitamin C, an ester of isovitamin C, or a salt of isovitamin C, preferably one or more of vitamin C, a sodium salt of vitamin C, a potassium salt of vitamin C, a calcium salt of vitamin C, a magnesium salt of vitamin C phosphate, a sodium salt of vitamin C, isovitamin C, a sodium salt of isovitamin C, a potassium salt of isovitamin C, a calcium salt of isovitamin C, a magnesium salt of isovitamin C phosphate, or a sodium salt of isovitamin C phosphate, and further preferably vitamin C, or isovitamin C. The weight ratio of the stabilizing agent to (6S)-5-methyl tetrahydrofolic acid or the salt thereof is 0.2-1000:1, and preferably 1-10:1.

A method for preparing the solid solution comprising (6S)-5-methyl tetrahydrofolic acid or a salt thereof and a stabilizing agent is provided. The method includes a method C or a method D.

The method C includes: reacting crude (6S)-5-methyl tetrahydrofolic acid or the high-purity (6S)-5-methyl tetrahydrofolic acid according to claim 1 with a stabilizing agent in water at pH 3-5 at a temperature of 50-90° C. directly, or reacting ultrasonically, and separating the solid that is crystallized out after reaction.

The method D includes: reacting crude (6S)-5-methyl tetrahydrofolic acid or the high-purity (6S)-5-methyl tetrahydrofolic acid according to claim 1, a stabilizing agent and a corresponding salt in water at pH 6-8 at a temperature of 50-90° C., or reacting ultrasonically, and separating the solid that is crystallized out after reaction.

The stabilizing agent is one or more selected from vitamin C, an ester of vitamin C, a salt of vitamin C, isovitamin C, an ester of isovitamin C, a salt of isovitamin C, dithiothreitol, reductive glutathione or zinc sulfate; and the corresponding salt is a chloride, and preferably calcium chloride, magnesium chloride, and zinc chloride In a preferred embodiment, during the reaction of the method C, the reaction temperature is 60-80° C., and the pH is 3-4 and adjusted with hydrochloric acid; and during the reaction of the method D, the reaction temperature is 60-80° C., and the pH is 7-7.5 and adjusted with sodium hydroxide A pharmaceutical composition is provided, which comprises:
a) the composition comprising (6S)-5-methyl tetrahydrofolic acid or a salt thereof, or the solid solution comprising (6S)-5-methyl tetrahydrofolic acid or a salt thereof and a stabilizing agent; and
b) a reducing agent, which is one or more selected from vitamin C, an ester of vitamin C, a salt of vitamin C, isovitamin C, an ester of isovitamin C, a salt of isovitamin C, mercaptoethanol, cysteine, mercaptoethane sulfonic acid, dithiothreitol, reductive glutathione, or zinc sulfate.

In an embodiment, the pharmaceutical composition is in the form of common tablets, sustained release tablets, controlled release tablets, effervescent tablets, granules, common capsules, sustained release capsules, controlled release capsules, dry suspensions, oral solutions, oral suspensions, injections, or freeze-dried powder injections.

In an embodiment, the weight ratio of the reducing agent to the (6S)-5-methyl tetrahydrofolic acid or the salt thereof in the pharmaceutical composition is 0.2-1000:1, and preferably 1-10:1.

Use of the high-purity (6S)-5-methyl tetrahydrofolic acid or a salt thereof, or the solid solution comprising (6S)-5-methyl tetrahydrofolic acid or a salt thereof and a stabilizing agent according to the present invention in the preparation of drugs for treating or preventing diseases associated with deficiency of 5-methyl tetrahydrofolic acid or a salt thereof in mammals.

DEFINITION OF TERMS

The terms used in the present invention have the following meanings, unless particularly specified otherwise.

Reversion refers to a phenomenon in which the impurity JK12A in (6S)-5-methyl tetrahydrofolic acid or a salt thereof is reversely converted into (6S)-5-methyl tetrahydrofolic acid or a salt thereof; and JK1303 is reversely converted into 5-methyl tetrahydropterioic acid.

Salting out is a means of improving the crystallization by adding a certain concentration of neutral salt to a solution containing a solid solute, thereby increasing the yield and quality.

Solid solution refers to a mixture formed by dispersing one or more solids uniformly in another solid.

Related substances refer to impurities introduced and produced during the production, use, and storage of (6S)-5-methyl tetrahydrofolic acid and salts thereof, including 4-aminobenzoylglutamic acid, JK12A, (6S)-Mefox, pyrazino-triazine derivatives, tetrahydrofolic acid, 7,8-dihydrofolic acid, folic acid, 5,10-methyl tetrahydrofolic acid, 5-methyl tetrahydropterioic acid, N2-methylamino-tetrahydrofolic acid, and salts thereof.

Purity refers to the proportion of the peak area of (6S)-5-methyl tetrahydrofolic acid to the total area of (6S)-5-methyl tetrahydrofolic acid and all the related substances in the liquid chromatogram.

Content as used herein refers to percentages by weight of a material, unless particularly specified otherwise.

In previous studies, attempts are made to remove the oxygen by adding some oxygen scavengers such as mercaptoethanol, ascorbic acid, sodium sulfite and so on, to the solution (6S)-5-methyltetrahydrofolic acid, thereby preventing sustained oxidative degradation. However, the use of these substances in production is unfeasible and unnecessary. In these studies, the purpose of oxygen removal can be achieved by the use of low concentrations of reducing agent. However, sufficient reversion of the oxidized impurities as described in this patent cannot be achieved with such a concentration. This is modified by the use of high concentrations of reducing agents in the METHOD JK.

The present inventors surprisingly find that the use of a high concentration of a reducing agent with moderate reducibility can achieve the reversion of most of the impurities produced from oxidative degradation, such as reversion of JK12A to (6S)-5-methyl tetrahydrofolic acid, and reversion of JK1303 to 5-methyl tetrahydropterioic acid. High-purity (6S)-5-methyl tetrahydrofolic acid or a salt thereof is crystallized out by means of salting out that follows. In this way, an incredibly high purity is obtained with a high yield, which has not been reported in the literature.

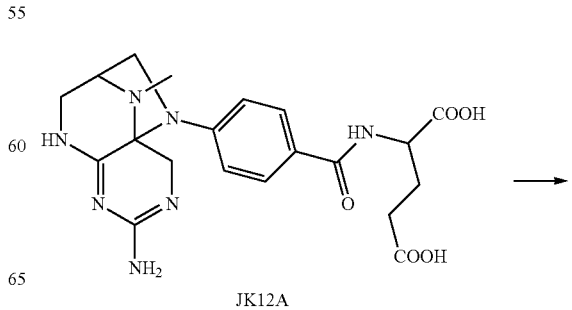

JK12A

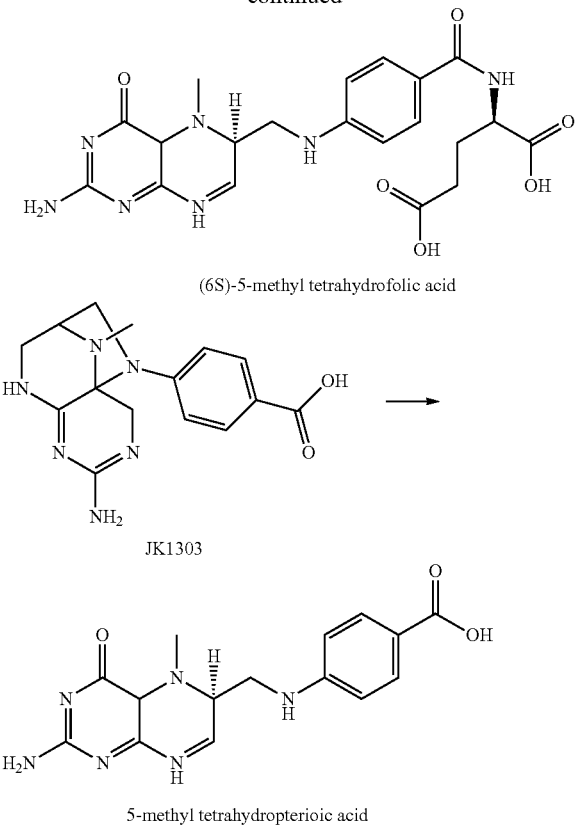

(6S)-5-methyl tetrahydrofolic acid

JK1303

5-methyl tetrahydropterioic acid (6S)-5-methyl tetrahydrofolic acid or a salt thereof having a purity of 98.0% or higher, or even approximate 100% can be prepared through this method. The content of related impurities including JK12A, JK1303, and 5-methyl tetrahydropterioic acid is greatly reduced even to a level below the detection limit of liquid chromatography, which is impossible to be achieved in the prior art.

The significance of the successful preparation of high-purity (6S)-5-methyl tetrahydrofolic acid and salts thereof lies not only in the significant progress in the manufacturing technology, but also in the correcting and avoiding of the consequences resulting from the previous misunderstanding with respect to the quality requirement for (6S)-5-methyl tetrahydrofolic acid and salts thereof due to the lack of research. With the gradual increase in the dosage of (6S)-5-methyl tetrahydrofolic acid, this will be more obvious. The concern in this regard can be explained by the fact that as for the acute toxicity test data published at present, the LD50 (median lethal dose) of calcium (6S)-5-methyltetrahydrofolate is 2000 mg/kg; and after the harmful impurities in the product are eliminated by using the technology of the present invention, the mice have no abnormal response at a dosage of 15000 mg/kg in a comparative test, so it is concluded that the maximum tolerable dose (MTD) is greater than 15 g/kg. Therefore, the contribution of the new technology to the product safety is self-evident The present invention also provides a method for preparing a composition of (6S)-5-methyl tetrahydrofolic acid or a salt thereof. The method comprises dissolving crude (6S)-5-methyl tetrahydrofolic acid or a salt thereof in water or an aqueous solvent, treating with a reverse reducing agent, to reverse most of the impurities produced from oxidative degradation into (6S)-5-methyl tetrahydrofolic acid or a salt thereof, and then crystallizing high-purity (6S)-5-methyl tetrahydrofolic acid or a salt thereof out by means of salting out or other process.

The reverse reducing agent useful in the present invention is as described above, and the reverse reducing agent for reversing the oxidized impurities needs to have suitable reducibility. If the reducibility is too high, reductive degradation is caused; and if the reducibility is too low, no desirable effect can be achieved.

In an embodiment, in the methods A and B and in the preparation of the composition above, the content of the reverse reducing agent in the solvent is not less than 2%, preferably not less than 20%, and further preferably not less than 40%, by weight.

The term salting out as used above has a meaning that is slightly different from that generally understood in biochemistry, but the effect is similar, in that the yield of crystals is increased, and the enrichment effect from the mother liquor for crystallization against the impurity is enhanced, so that the purity of the product reaches an incredible level.

The salting-out agent serving for salting out used in the present invention includes, in addition to the reducing agent above, a commonly used salt, for example neutral inorganic salts such as sodium chloride, potassium chloride, and magnesium sulfate. In the present invention, the salting-out effect is preferably achieved by increasing the concentration of the reducing agent.

Moreover, in a liquid chromatogram of the solid solution comprising (6S)-5-methyl tetrahydrofolic acid or a salt thereof and a stabilizing agent provided in the present invention, total content of the stabilizing agent and (6S)-5-methyl tetrahydrofolic acid or the salt thereof is greater than 99.5%, preferably greater than 99.8%, and further preferably greater than 99.9%. The content is calculated based on the peak area in the liquid chromatogram.

The solid solution has an excellent homogeneous dispersion, and can effectively protect the active ingredient of the present invention.

In the solid solution of the present invention, the (6S)-5-methyl tetrahydrofolic acid and the stabilizing agent are kept highly homogeneous, thus ensuring the stabilization effect. In a typical embodiment, the (6S)-5-methyl tetrahydrofolic acid calcium salt is of crystal form C with uniform and fine particles and narrow particle size distribution, and can form a highly homogeneous solid solution with the stabilizing agent. This is difficult to be achieved in the prior art.

In a preferred embodiment, the solid solution of the present invention is a solid solution of (6S)-5-methyl tetrahydrofolic acid or a salt with vitamin C, isovitamin C, zinc sulfate, reductive glutathione, dithiothreitol or a salt thereof.

In a typical case, the solid solution prepared according to the present invention has only two typical absorption peaks in the HPLC chromatogram, and is thus highly neat.

The stabilizing agent and the (6S)-5-methyl tetrahydrofolic acid are homogeneously dispersed in the solid solution, thus achieving a better stabilization effect.

In the solid solution product of the present invention, an additional stabilizing agent may be added, and other additives may also be added as desired.

The present invention further provides another method for preparing a solid solution. The method comprises dissolving (6S)-5-methyl tetrahydrofolic acid or a salt thereof in water or an aqueous solvent, adding a stabilizing agent to reverse the impurities, and then crystallizing the stabilizing agent and (6S)-5-methyl tetrahydrofolic acid or a salt thereof out, filtering, and drying. Further, (6S)-5-methyl tetrahydrofolic acid and the stabilizing agent are dispersed in water, sodium hydroxide is added dropwise, and dissolved by stirring, then a corresponding salt is added for crystallization, and the crystal is filtered out and dried.

The present invention further provides a safe method of using (6S)-5-methyl tetrahydrofolic acid or a salt thereof. The method comprises a. making use of the composition comprising (6S)-5-methyl tetrahydrofolic acid or a salt thereof, or the solid solution; and b. adding a pharmaceutically acceptable reductive substance as the stabilizing agent.

In a preferred safe method of using (6S)-5-methyl tetrahydrofolic acid or a salt thereof, the stabilizing agent is selected from vitamin C and an ester and salt thereof, isovitamin C and an ester and salt thereof, dithiothreitol, reductive glutathione, and zinc sulfate; preferably vitamin C and an ester and salt thereof, and isovitamin C and an ester and salt thereof; further preferably a sodium salt, a potassium salt, and a calcium salt of vitamin C and isovitamin C, a magnesium salt of vitamin C phosphate, and a sodium salt of vitamin C phosphate; and most preferably vitamin C and isovitamin C.

In a preferred safe method of using (6S)-5-methyl tetrahydrofolic acid or a salt thereof, the stabilizing agent is combined with (6S)-5-methyl tetrahydrofolic acid by directly mixing them in the form of solids, or by dissolving them in a solvent and then crystallizing out together, or by preparing them into a cocrystal or a solid solution, and preferably by preparing them into a solid solution.

In the safe method of using (6S)-5-methyl tetrahydrofolic acid or a salt thereof, the use of the stabilizing agent interrupts the further progression of the oxidation of (6S)-5-methyl tetrahydrofolic acid and the salt thereof. By means of this solution, the negative effect of JK12A and other harmful degradation products on human can be effectively controlled, and the dosage can be accurately controlled. This safe method of using is also referred to as METHOD JK. In the METHOD JK, the safety characteristics of (6S)-5-methyl tetrahydrofolic acid can also be ameliorated by using the two portions separately.

In a preferred safe method of using (6S)-5-methyl tetrahydrofolic acid or a salt thereof, the weight ratio of the stabilizing agent to (6S)-5-methyl tetrahydrofolic acid is 0.2-1000:1; and further preferably 1-10:1.

In the safe method of using (6S)-5-methyl tetrahydrofolic acid or a salt thereof described in the present invention, vitamin C and a salt thereof serve as the reducing agent, the salting-out agent, and the stabilizing agent in a preferred embodiment. In other words, vitamin C and the salt thereof are the reducing agent for reversing the oxidized impurities, the salting-out agent used in the purification process, and also the stabilizing agent for (6S)-5-methyl tetrahydrofolic acid. Vitamin C and the salt thereof remaining during production have no need to be removed dedicatedly. In a subsequent process, a desired amount of vitamin C is added when necessary. Also, similar effect can be achieved by using reductive glutathione, zinc sulfate and a single isomer thereof, dithiothreitol, isovitamin C, and so on. Logically, these substances can be suitably used as the reducing agent, the salting-out agent, and the stabilizing agent alone.

The safe method of using (6S)-5-methyl tetrahydrofolic acid or a salt thereof is employed in the production of a preparation comprising (6S)-5-methyl tetrahydrofolic acid alone or in combination with other active ingredients. The preparation is preferably in the form of common tablets, sustained release tablets, controlled release tablets, effervescent tablets, granules, common capsules, sustained release capsules, controlled release capsules, dry suspensions, oral solutions, oral suspensions, injections, and freeze-dried powder injections, and further preferably in the form of common tablets, common capsules, oral solutions, injections, and freeze-dried powder injections.

Use of the safe method of using (6S)-5-methyl tetrahydrofolic acid or a salt thereof in the preparation of drugs for treating or preventing diseases associated with deficiency of 5-methyl tetrahydrofolic acid or a salt thereof in mammals.

The present invention also provides use of the safe method of using (6S)-5-methyl tetrahydrofolic acid or a salt thereof in the preparation of drugs for treating or preventing diseases associated with deficiency of 5-methyl tetrahydrofolic acid or a salt thereof in mammals including, for example, subacute encephalitis associated with dementia and vacuolar myelopathy, cerebral folate deficiency, pathophysiology of vascular and cardiovascular diseases such as premature obstructive arterial disease, severe vascular disease in infancy and childhood, progressive arterial stenosis, intermittent claudication, renal vascular hypertension, ischemic cerebrovascular disease, premature retinal artery and vein occlusion, cerebral occlusive arterial disease, occlusive peripheral arterial disease, and premature death due to thromboembolic disease and/or ischemic heart disease; autoimmune diseases such as psoriasis, celiac disease, arthritis and inflammatory conditions; magaloblastic anemia due to folate deficiency, and intestinal absorption disorders; as antidotes for folic acid antagonists (such as methotrexate, pyrimethamine or trimethoprim, etc.); for preventing the severe toxic effects caused by treatment with over or high dose of methotrexate; for reducing the risk of abortion and/or giving birth to fetuses with neural tube defects, cleft lip and/or cleft palate defects; for maintaining normal homocysteine level and/or metabolism thereof; changes in synthesis and functions of DNA and RNA, and in cell synthesis; and depression.

The principle underlying the selection of the reducing agent, the salting-out agent and the stabilizing agent of the present invention includes primarily chemical safety such that the product will not be degraded; and secondarily relative safety in physiology. The substance that is fully validated in food and medical science is preferred. It should be understood that the amount of the reducing agent, the salting-out agent, and the stabilizing agent is required to exceed a minimum amount, otherwise it may cause the fact that the impurities cannot be sufficiently reversed, the salting-out effect is poor and/or the stabilization effect is poor. It should also be understood that in general, there is no strict upper limit on the amount of the reducing agent and the stabilizing agent.

The impurities contained in (6S)-5-methyl tetrahydrofolic acid and a salt thereof according to the present invention include JK12A and 5-methyl tetrahydropterioic acid having the following structures:

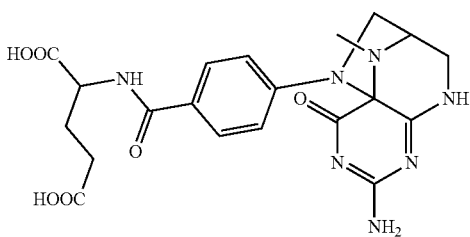

JK12A

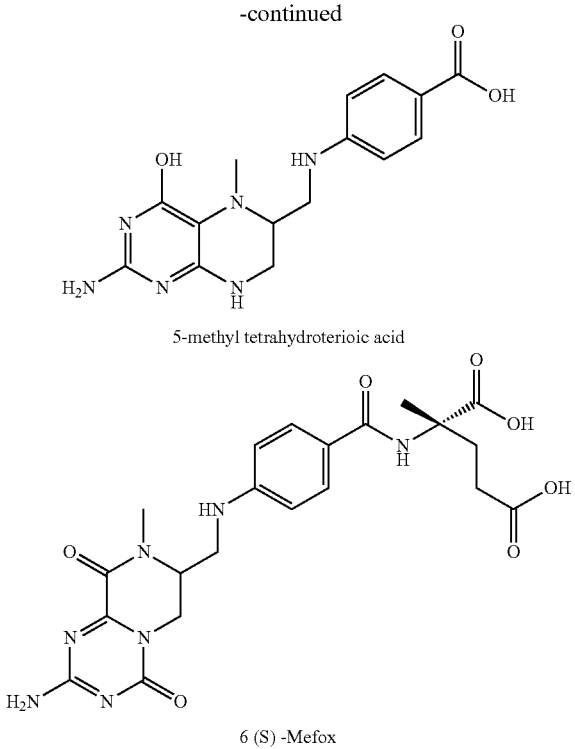

5-methyl tetrahydroterioic acid 6 (S) -Mefox

After oxidation, 5-methyl tetrahydropterioic acid is converted into JK1303 having serious kidney toxicity with a high yield, and thus need to be controlled strictly.

The present invention has the following beneficial effects. The present invention provides high-purity (6S)-5-methyl tetrahydrofolic acid or a salt thereof, the preparation method therefor, the solid solution comprising high-purity (6S)-5-methyl tetrahydrofolic acid or a salt thereof, the preparation method therefor, and the safe method of using (6S)-5-methyl tetrahydrofolic acid or a salt thereof. In all these embodiments, the harmful chemicals possibly generated in a product of (6S)-5-methyl tetrahydrofolic acid or a salt thereof are reversed into the product itself by the use of a pharmaceutically acceptable reducing agent, thus achieving the purpose of using (6S)-5-methyl tetrahydrofolic acid or a salt thereof safely.

BRIEF DESCRIPTION OF THE DRAWINGS

FIG. 1 is a partially enlarged view of a large number of vacuoles anatomically found after severe renal tubular necrosis of the mice 14 days after administration of JK1303.

DETAILED DESCRIPTION

For better understanding of the technical solutions of the present invention, the technical solutions of the present invention will be further described below with reference to specific embodiments; however the present invention is not limited thereto.

The conditions used for detection by HPLC in the present invention are as follows.

Chromatographic Conditions:

| Chromatographic column | C18-250 * 4.6 mm-5 μm |
| --- | --- |
| Detection wavelength | UV at 280 nm |
| Flow rate | 1.0 ml/min |
| Injection volume | 20 μl |
| Column temperature | 30° C. |

Formulation of Mobile Phases

Mobile phase A: 7.80 g of $NaH_2PO_4.2H_2O$ was weighed, dissolved in 1000 ml of water, and adjusted to pH 6.5 with a 32% NaOH solution.

Mobile phase B: 5.07 g of $NaH_2PO_4.2H_2O$ was weighed, dissolved in 650 ml of water, added with 350 ml of methanol, and adjusted to pH 8.0 with a 32% NaOH solution.

Gradient Program:

| T (min) | A % | B % |
| --- | --- | --- |
| 0 | 100 | 0 |
| 14 | 45 | 55 |
| 17 | 0 | 100 |
| 22 | 0 | 100 |
| 31 | 100 | 0 |

Preparation of Sample Solution:

A suitable amount of a sample was dissolved in cold water at 2-8° C. (which was prepared by adding sodium sulfite under nitrogen atmosphere, distilling, collecting, and storing, and cooled to 2-8° C.) under nitrogen atmosphere, to formulate a solution of about 0.5 mg/ml. The solution was prepared in situ when used.

In some example of the present invention, ultrasonic waves are used as an aid, which can obviously accelerate the reversion and crystallization.

For ease of description, the data detected in the examples is only with respect to 5-methyl tetrahydrofolic acid, salts thereof, and related substances.

EXAMPLE 1

Preparation of JK12A

Under nitrogen atmosphere, 10 g of (6S)-5-methyl tetrahydrofolic acid was transferred to a reaction flask, and 80 g of water was added, and adjusted to pH 7.3 with a 10% sodium hydroxide solution with stirring. After the solid was completely dissolved, 5 g of activated carbon was added, and reacted overnight with stirring in open reactor. After the raw material was detected to be reacted completely by HPLC, the reaction solution was filtered, and the filtrate was adjusted to pH 4.0 with 50% acetic acid. A crystal was formed, and filtered. The filter cake was washed respectively with ethanol and acetone, and dried under vacuum, to obtain 6.0 g of JK12A as a yellow solid (chemical purity 99.42%).

EXAMPLE 2

Preparation of 5-methyl Tetrahydropterioic Acid 61 g of (6S)-5-methyl tetrahydrofolic acid was slowly added to 600 ml of a 25% sodium hydroxide solution in water, heated to reflux, and reacted overnight. After the raw material was reacted completely, the reaction solution was cooled to room temperature, and the impurities were filtered off. The filtrate was adjusted to pH 9-10 with concentrated sulfuric acid, and the impurities were precipitated out. The reaction solution was cooled to 10-15° C., and filtered. The filtrate was further adjusted to pH 2 with concentrated sulfuric acid, and a solid was precipitated out, stirred for 0.5 hr at 60° C., and filtered while hot. The solid was washed with water, and dried, to obtain 44 g of a white solid (purity 96%).

EXAMPLE 3

Preparation of JK1303

5 g of (6S)-5-methyl tetrahydropterioic acid was fed to a three-neck flask, 50 g of water was added, stirred fully, and adjusted to pH 9.0 with a 10% sodium hydroxide solution. After the solid was completely dissolved, 3 g of activated carbon was added, the oxygen balloon was closed, and the stirring was continued overnight. The reaction solution was filtered, and the filter cake was washed with water. The filtrate was adjusted to pH 4 with a 50% acetic acid solution in water, and the crystallization was continued for 30 min with stirring. After filtering, the filter cake was washed twice with water, slurried twice in 30 ml acetone, and dried at 30° C. under vacuum, to obtain 3.04 g of a product (purity by HPLC: 94.3%).

EXAMPLE 4

Reversion of JK12A 10 g of water was added to 0.1 g of JK12A (purity by HPLC: 95.91%), and adjusted to pH 7.2 with 10% sodium hydroxide with stirring. After the solid was completely dissolved, 0.8 g of dithiothreitol was slowly added, and stirred for 1 hr. The reaction solution was sampled and detected to contain 97.53% of 5-methyl tetrahydrofolic acid and 0.72% of JK12A residue.

EXAMPLE 5

Reversion of JK12A 10 g of water was added to 0.1 g of JK12A (purity by HPLC: 95.91%), and adjusted to pH 7.2 with 10% sodium hydroxide with stirring. After the solid was completely dissolved, 0.5 g of cysteine was slowly added, and stirred for 1 hrs. The reaction solution was sampled and detected to contain 96.64% of 5-methyl tetrahydrofolic acid and 0.85% of JK12A residue.

EXAMPLE 6

Reversion of JK12A 0.1 g of JK12A (purity by HPLC: 74.04%) and 0.2 g of mercaptoethanol were added to 5 ml of water, and adjusted to pH 7.5 with 30% sodium hydroxide with stirring. After the solid was completely dissolved, stirring was further continued for 1 hr. Then the reaction solution was sampled and detected to contain 60.92% of 5-methyl tetrahydrofolic acid and 0.59% of JK12A residue.

EXAMPLE 7

Reversion of JK12A 0.1 g of JK12A (purity by HPLC: 74.04%) and 0.2 g of sodium mercaptoethane sulfonate were added to 5 ml of water, and adjusted to pH 7.5 with 30% sodium hydroxide with stirring. After the solid was completely dissolved, stirring was further continued for 1 hr. Then the reaction solution was sampled and detected to contain 72.85% of 5-methyl tetrahydrofolic acid and 0.61% of JK12A residue.

EXAMPLE 8

Preparation and Conversion of Mixture Comprising (6S)-Mefox and JK12A

Under nitrogen atmosphere, 1 g of (6S)-5-methyl tetrahydrofolic acid was transferred to a reaction flask, and 8 g of water was added, stirred, and adjusted to pH 7.3 with a 10% sodium hydroxide solution. After the solid was completely dissolved, 3 g of activated carbon was added, and reacted for 10 hrs with stirring in open reactor. The reaction solution was detected by HPLC to contain 12.20% of 5-methyl tetrahydrofolic acid; 83.51% of JK12A, and 0.57% of (6S)-Mefox), and filtered. The filtrate was added with 10 g of vitamin C, and the pH was adjusted to and maintained at 7.0 with caustic soda liquid. After stirring for 3 hrs at 60° C., the reaction solution was sampled and detected to contain 96.49% of 5-methyl tetrahydrofolic acid; 0% of JK12A; and 0% of (6S)-Mefox

EXAMPLE 9

Reversion of JK1303

10 g of water was added to 0.1 g of JK1303 (purity by HPLC: 96.7%), and adjusted to pH 7.0 with 10% sodium hydroxide with stirring. After the solid was completely dissolved, 1 g of sodium vitamin C was slowly added, and stirred for 1 hr. The reaction solution was sampled and detected to contain 96.6% of 5-methyl tetrahydropterioic acid and 0% of JK1303 residue.

EXAMPLE 10

Composition Comprising (6S)-5-methyl Tetrahydrofolic Acid Calcium Salt 50 ml of water and 50 g of vitamin C were neutralized to pH 7.0 with sodium hydroxide, and the solution became clear after the solid was completely dissolved. 1 g of crude (6S)-5-methyl tetrahydrofolic acid calcium salt was added batchwise, and ultrasonicated at 65° C. for 2 hrs. After filtering, washing, and drying under vacuum, 0.72 g of a composition comprising (6S)-5-methyl tetrahydrofolic acid calcium salt was obtained.

| Related substance | Crude (6S)-5-methyl tetrahydrofolic acid calcium salt/content | Final product/content |
|---|---|---|
| JK12A | 0.49% | — |
| 5-methyl tetrahydrofolic acid | 99.26% | 99.9% |
| 5-methyl tetrahydropterioic acid | 0.14% | — |
| Other impurities | 0.11% | 0.01 |

EXAMPLE 11

Composition Comprising (6S)-5-methyl Tetrahydrofolic Acid Calcium Salt 15 g of (6S)-5-methyl tetrahydrofolic acid and 150 g of vitamin C were added to 225 ml of water, and neutralized to pH 7.0 with a 30% sodium hydroxide solution in water. The solid was dissolved, and the solution was stirred for 1 hr. Then 15 g of a 40% calcium chloride solution in water was added and ultrasonicated at 70° C. for crystallization. After 3 hrs, white particles were crystallized out, filtered, and then washed with water. The filter cake was dried under vacuum, to obtain 10.1 g of a solid composition comprising (6S)-5-methyl tetrahydrofolic acid calcium salt.

| Related substance | Crude (6S)-5-methyl tetrahydrofolic acid/content | Final product/content |
|---|---|---|
| JK12A | 0.22% | 0.03% |
| (6S)-Mefox | 0.02% | 0.01% |
| 5-methyl tetrahydrofolic acid | 99.40% | 99.95% |
| 5-methyl tetrahydropterioic acid | 0.03% | — |
| Other impurities | 0.33% | 0.01% |

EXAMPLE 12

Composition Comprising (6S)-5-methyl Tetrahydrofolate 1 g of (6S)-5-methyl tetrahydrofolic acid, 1 g of vitamin C, and 0.5 g of NaCl were added to 10 ml of water, and neutralized to pH 7.0 with a 30% sodium hydroxide solution in water. The solid was dissolved, and the solution was stirred for 1 hr. Then 1 g of a 40% calcium chloride solution in water was added and ultrasonicated at 70° C. After 1 hr, a solid was crystallized out, filtered, and then washed. The filter cake was dried under vacuum, to obtain 0.52 g of a solid composition comprising (6S)-5-methyl tetrahydrofolic acid calcium salt.

| Related substance | Crude (6S)-5-methyl tetrahydrofolic acid/content | Final product/content |
|---|---|---|
| JK12A | 0.22% | 0.07% |
| (6S)-Mefox | 0.02% | 0.01% |
| 5-methyl tetrahydrofolic acid | 99.40% | 99.75% |
| 5-methyl tetrahydropterioic acid | 0.03% | — |
| Other impurities | 0.33% | 0.15% |

EXAMPLE 13

Composition Comprising (6S)-5-methyl Tetrahydrofolic Acid Calcium Salt 0.5 g of (6S)-5-methyl tetrahydrofolic acid, 10 mg of vitamin C, and 0.1 g of sodium chloride were added to 10 ml of water, and neutralized to pH 7.5 with a 30% sodium hydroxide solution in water. The solution became clear after the solid was completely dissolved. The reaction solution was stirred for 1 hr under nitrogen atmosphere. 1 g of a 20% calcium chloride solution in water was added, and ultrasonicated at 70° C. for crystallization. After 1.0 hr, white particles were crystallized out, filtered, and then washed. The filter cake was dried under vacuum, to obtain 0.38 g of a solid composition comprising (6S)-5-methyl tetrahydrofolic acid calcium salt.

| Related substance | Crude (6S)-5-methyl tetrahydrofolic acid/content | Final product/content |
|---|---|---|
| JK12A | 0.22% | 0.09% |
| (6S)-Mefox | 0.02% | |
| 5-methyl tetrahydrofolic acid | 99.40% | 99.63% |
| 5-methyl tetrahydropterioic acid | 0.03% | — |
| Other impurities | 0.33% | 0.27% |

EXAMPLE 14

Composition Comprising (6S)-5-methyl Tetrahydrofolic Acid Calcium Salt 1 g of (6S)-5-methyl tetrahydrofolic acid and 3 g of isovitamin C were added to 20 ml of water, and neutralized to pH 7.0 with a 30% sodium hydroxide solution in water. The solution became clear after the solid was completely dissolved. The reaction solution was stirred for 1 hr, and then 1 g of a 40% calcium chloride solution in water was added, and ultrasonicated at 60° C. After 1 hr, a solid were crystallized out, filtered, and then washed. The filter cake was dried under vacuum, to obtain 0.80 g of a composition comprising (6S)-5-methyl tetrahydrofolic acid calcium salt.

| Related substance | Crude (6S)-5-methyl tetrahydrofolic acid/content | Final product/content |
|---|---|---|
| JK12A | 0.22% | — |
| (6S)-Mefox | 0.02% | 0.05% |
| 5-methyl tetrahydrofolic acid | 99.40% | 99.75% |
| 5-methyl tetrahydropterioic acid | 0.03% | — |
| Other impurities | 0.33% | 0.18% |

EXAMPLE 15

Composition Comprising (6S)-5-methyl Tetrahydrofolic Acid 0.5 g of the composition comprising calcium (6S)-5-methyl tetrahydrofolate prepared in EXAMPLE 11 was heated to 40° C., and adjusted to pH 4.0 with a hydrochloric acid solution. The system was stirred for 1 hr for crystallization while the pH was maintained unchanged. After cooling to room temperature, filtering, washing, and drying at 25° C. under vacuum, 0.23 g of a composition comprising (6S)-5-methyl tetrahydrofolic acid was obtained, which contains 99.80% of (6S)-5-methyl tetrahydrofolic acid, 0% of JK12A, 0.07% of (6S)-Mefox, and 0% of 5-methyl tetrahydropterioic acid, as detected by HPLC.

| Related substance | Composition of (6S)-5-methyl tetrahydrofolic acid calcium salt/content | Final product/content |
| --- | --- | --- |
| JK12A | 0.03% | — |
| (6S)-Mefox | 0.01% | — |
| 5-methyl tetrahydrofolic acid | 99.95% | 99.80% |
| 5-methyl tetrahydropterioic acid | — | — |
| Other impurities | 0.01% | 0.20% |

EXAMPLE 16

Composition Comprising 6R,S-5-methyl Tetrahydrofolic Acid Calcium Salt 1 g of 6R,S-5-methyl tetrahydrofolic acid and 10 g of vitamin C were added to 15 ml of water, and neutralized to pH 7.0 with a 30% sodium hydroxide solution in water. The solution became clear after the solid was completely dissolved. 1 g of a 40% calcium chloride solution in water was added, and ultrasonicated at 70° C. for crystallization. After filtering, washing with water, and drying under vacuum, 0.54 g of a composition comprising 6R,S-5-methyl tetrahydrofolate was obtained.

| Related substance | Crude 6R, S-5-methyl tetrahydrofolate/content | Final product/content |
| --- | --- | --- |
| JK12A | 0.21% | — |
| (6S)-Mefox | — | — |
| 5-methyl tetrahydrofolic acid | 99.15% | 99.59% |
| 5-methyl tetrahydropterioic acid | 0.28% | 0.08% |
| Other impurities | 0.36% | 0.33% |

EXAMPLE 17

Composition Comprising Sodium 6R,S-5-methyl Tetrahydrofolic Acid 1 g of 6R,S-5-methyl tetrahydrofolic acid, and 5 g of vitamin C were added to 20 ml of water, and neutralized to pH 7.0 with a 30% sodium hydroxide solution in water. The solution became clear after the solid was completely dissolved. The reaction was continued for 2 hrs at 60° C. with oxygen being isolated. Then, the reaction solution was added dropwise to 200 ml of ethanol, to crystallize a sodium salt out, which was filtered, washed, and dried under vacuum, to obtain 0.52 g of a composition comprising sodium 6R,S-5-methyl tetrahydrofolate.

| Related substance | Crude 6R, S-5-methyl tetrahydrofolic acid/content | Final product/content |
| --- | --- | --- |
| JK12A | 0.21% | — |
| (6S)-Mefox | — | — |
| 5-methyl tetrahydrofolic acid | 99.15% | 99.64% |
| 5-methyl tetrahydropterioic acid | 0.28% | 0.12% |
| Other impurities | 0.36% | 0.34% |

EXAMPLE 18

Composition Comprising of (6S)-5-methyl Tetrahydrofolic Acid Arginine Salt 5 g of vitamin C was added to 5 ml of water, and neutralized to pH 7.0 with sodium hydroxide. The solution became clear after the solid was completely dissolved. 0.5 g of crude (6S)-5-methyl tetrahydrofolic acid arginine salt was added, dissolved completely, and ultrasonically stirred for 2 hrs at 60° C. The reaction solution was added dropwise to 50 ml of ethanol, and stirred to crystallize a solid out. The solid was filtered out and detected. 0.26 g of a composition comprising (6S)-5-methyl tetrahydrofolic acid arginine salt was obtained.

| Related substance | Crude 5-methyl tetrahydrofolic acid arginine salt/content | Final product/content |
| --- | --- | --- |
| JK12A | 0.76% | — |
| (6S)-Mefox | 1.30% | 0.27% |
| 5-methyl tetrahydrofolic acid | 97.69% | 99.70% |
| 5-methyl tetrahydropterioic acid | 0.05% | — |
| Other impurities | 0.20% | 0.03% |

EXAMPLE 19

Composition Comprising (6S)-5-methyl Tetrahydrofolic Acid D-Glucosamine Salt 5 g of vitamin C was added to 10 ml of water, and neutralized to pH 7.0 with sodium hydroxide. The solution became clear after the solid was completely dissolved. 2.0 g of crude (6S)-5-methyl tetrahydrofolic acid D-glucosamine salt was added, dissolved completely, and ultrasonically stirred for 2 hrs at 60° C. Ethanol was slowly added dropwise, and a solid was crystallized out, which was filtered and recrystallized in ethanol, to obtain a composition comprising (6S)-5-methyl tetrahydrofolic acid D-glucosamine salt.

| Related substance | Crude 5-methyl tetrahydrofolic acid D-glucosamine salt/content | Final product/content |
| --- | --- | --- |
| JK12A | 0.56% | — |
| (6S)-Mefox | 0.70% | 0.14 |
| 5-methyl tetrahydrofolic acid D-glucosamine salt | 98.47% | 99.81% |
| 5-methyl tetrahydropterioic acid | 0.05% | — |
| Other impurities | 0.22% | 0.05% |

EXAMPLE 20

Solid Solution Comprising (6S)-5-methyl Tetrahydrofolic Acid Calcium Salt and Vitamin C 1 g of (6S)-5-methyl tetrahydrofolic acid and 2.0 g of vitamin C were added to 20 ml of water, and neutralized to pH 7.5 with a 30% sodium hydroxide solution in water. The solid was dissolved, and the solution was stirred for 1 hr. Then 1 g of a 40% calcium chloride solution in water was added and ultrasonicated at 70° C. for crystallization. After 1.0 hr, white particles were crystallized out, filtered, dried, and detected by HPLC to comprise 94.89% of (6S)-5-methyl tetrahydrofolic acid calcium salt, and 5.11% of vitamin C.

EXAMPLE 21

Solid Solution Comprising (6S)-5-methyl Tetrahydrofolic Acid Calcium Salt and Isovitamin C 0.1 g of (6S)-5-methyl tetrahydrofolic acid and 0.3 g of isovitamin C were added to 1.5 ml of water, and neutralized to pH 7.5 with a 30% sodium hydroxide solution in water. The solid was dissolved, and the solution was stirred for 1 hr. Then 1 g of a 40% calcium chloride solution in water was added and ultrasonicated at 90° C. for crystallization. After 1.0 hr, white particles were crystallized out, which were filtered, dried, and detected by HPLC to comprise 29.29% of (6S)-5-methyl tetrahydrofolic acid calcium salt, and 70.66% of isovitamin C.

EXAMPLE 22

Solid Solution Comprising (6S)-5-methyl Tetrahydrofolic Acid Calcium Salt and Zinc Sulfate 0.5 g of (6S)-5-methyl tetrahydrofolic acid and 1.0 g of zinc sulfate were added to 10 ml of water, and neutralized to pH 7.5 with a 30% sodium hydroxide solution in water. The solid was dissolved, and the solution was stirred for 1 hr. Then 1 g of a 20% calcium chloride solution in water was added and ultrasonicated at 70° C. for crystallization. After 1.0 hr, a solid solution was obtained, which was filtered, dried, and detected by HPLC (with an ELSD detector) to comprise 27.69% of (6S)-5-methyl tetrahydrofolic acid calcium salt, and 72.26% of zinc sulfate.

EXAMPLE 23

Solid Solution Comprising 5-methyl Tetrahydrofolic Acid Calcium Salt and Reductive Glutathione 0.5 g of (6S)-5-methyl tetrahydrofolic acid and 1.5 g of reductive glutathione were added to 10 ml of water, and neutralized to pH 7.5 with a 30% sodium hydroxide solution in water. The solid was dissolved, and the solution was stirred for 1 hr. Then 1 g of a 20% calcium chloride solution in water was added and ultrasonicated at 70° C. for crystallization. After 1.0 hr, white particles were crystallized out, which were filtered, dried, and detected by HPLC (with an ELSD detector) to comprise 37.62% of (6S)-5-methyl tetrahydrofolic acid calcium salt, and 62.33% of reductive glutathione.

EXAMPLE 24

Solid Solution Comprising (6S)-5-methyl Tetrahydrofolic Acid and Vitamin C 0.5 g of (6S)-5-methyl tetrahydrofolic acid and 3.0 g of vitamin C were added to 10 ml of water, and neutralized to pH 7.5 with a 30% sodium hydroxide solution in water. The solid was dissolved, and the solution was stirred for 1 hr. A suitable amount of 6N hydrochloric acid solution in water was added dropwise, to adjust the pH to 4.0, and stirred 50° C. for crystallization. After 1.0 hr, white particles were crystallized out, which were filtered, dried, and detected by HPLC to comprise 26.80% of (6S)-5-methyl tetrahydrofolic acid and 73.17% of vitamin C.

EXAMPLE 25

Solid Solution Comprising (6S)-5-methyl Tetrahydrofolic Acid Zinc Salt and Vitamin C 0.5 g of (6S)-5-methyl tetrahydrofolic acid and 1.5 g of vitamin C were added to 10 ml of water, and neutralized to pH 7.5 with a 20% sodium hydroxide solution in water. The solution became clear after the solids were completely dissolved. 0.8 g of a 50% zinc chloride solution in water was added, crystallized for 2 hrs, and filtered under nitrogen atmosphere. The filter cake was dried under vacuum and detected by HPLC to comprise 88.7% of (6S)-5-methyl tetrahydrofolic acid zinc salt, and 11.0% of vitamin C.

EXAMPLE 26

Solid Solution of (6S)-5-methyl Tetrahydrofolic Acid Calcium Salt, and Magnesium Vitamin C Phosphate 0.5 g of (6S)-5-methyl tetrahydrofolic acid, and 2.0 g of magnesium vitamin C phosphate were added to 10 ml of water, and neutralized to pH 7.5 with a 20% sodium hydroxide solution in water. The solution became clear after the solids were completely dissolved. 0.6 g of a 50% calcium chloride solution in water was added, and then reacted ultrasonically at 70° C. After 1.5 h, white particles were crystallized out, which were filtered under nitrogen atmosphere, dried and detected by HPLC to comprise 62.4% of (6S)-5-methyl tetrahydrofolic acid calcium salt, and 37.4% of vitamin C.

EXAMPLE 27

Stability of Composition Comprising (6S)-5-methyl Tetrahydrofolic Acid Calcium Salt Prepared Through METHOD JK and Vitamin C 1 g of the composition of (6S)-5-methyl tetrahydrofolic acid calcium salt obtained in Example 11 was fully mixed by grinding with vitamin C in various proportions by weight, placed in an incubator at 25° C. and 40% humidity, and detected for (6S)-5-methyl tetrahydrofolic acid calcium salt and JK12A periodically.

| Days | Amount of VC | | | | | |
|---|---|---|---|---|---|---|
| | 0 | | 20% | | 100% | |
| | (6S)-5-methyl tetrahydrofolic acid calcium salt | JK1 2A | (6S)-5-methyl tetrahydrofolic acid calcium salt | JK1 2A | (6S)-5-methyl tetrahydrofolic acid calcium salt | JK1 2A |
| 0 | 99.95% | 0.03% | 99.95% | 0.03% | 99.95% | 0.03% |
| 7 | 99.90% | 0.06% | 99.94% | 0.04% | 99.94% | 0.03% |
| 15 | 99.85% | 0.12% | 99.89% | 0.08% | 99.90% | 0.05% |
| 30 | 99.63% | 0.25% | 99.71% | 0.17% | 99.90% | 0.05% |
| 60 | 99.40% | 0.46% | 99.50% | 0.22% | 99.86% | 0.10% |

| Days | Amount of VC | | | | | |
|---|---|---|---|---|---|---|
| | 500% | | 1000% | | 10000% | |
| | (6S)-5-methyl tetrahydrofolic acid calcium salt | JK1 2A | (6S)-5-methyl tetrahydrofolic acid calcium salt | JK1 2A | (6S)-5-methyl tetrahydrofolic acid calcium salt | JK1 2A |
| 0 | 99.95% | 0.03% | 99.95% | 0.03% | 99.95% | 0.03% |
| 7 | 100.00% | — | 100.00% | — | 100.00% | — |
| 15 | 100.00% | — | 100.00% | — | 100.00% | — |
| 30 | 99.98% | — | 100.00% | — | 100.00% | — |
| 60 | 99.96% | — | 100.00% | — | 100.00% | — |

What is claimed is:

1. A solid solution consisting essentially of (6S)-5-methyl tetrahydrofolic acid or a salt thereof and a stabilizing agent selected from the group consisting of vitamin C, an ester of vitamin C, a salt of vitamin C, isovitamin C, an ester of isovitamin C, a salt of isovitamin C, dithiothreitol, reductive glutathione, and zinc sulfate, wherein the total content of the stabilizing agent and (6S)-5-methyl tetrahydrofolic acid or the salt thereof in the solid solution as determined from a liquid chromatogram of the solid solution is greater than 99.5%, and the weight ratio of the stabilizing agent to the (6S)-5-methyl tetrahydrofolic acid or the salt thereof is from 1:1 to 10:1.

2. The solid solution according to claim 1, wherein the total content of the stabilizing agent and (6S)-5-methyl tetrahydrofolic acid or the salt thereof as determined from the liquid chromatogram of the solid solution is greater than 99.8%.

3. The solid solution according to claim 1, wherein the stabilizing agent is one or more selected from the group consisting of vitamin C, an ester of vitamin C, a salt of vitamin C, isovitamin C, an ester of isovitamin C, and a salt of isovitamin C.

4. A method for preparing the solid solution comprising (6S)-5-methyl tetrahydrofolic acid or a salt thereof and a stabilizing agent according to claim 1, the method comprising a method C or a method D, wherein the method C comprises reacting crude (6S)-5-methyl tetrahydrofolic acid or a high-purity (6S)-5-methyl tetrahydrofolic acid with a stabilizing agent in water at pH 3-5 at a temperature of 50-90° C. directly, or reacting ultrasonically, and separating the solid that is crystallized out after reaction; and the method D comprises reacting crude (6S)-5-methyl tetrahydrofolic acid or a high-purity (6S)-5-methyl tetrahydrofolic acid a stabilizing agent and a corresponding salt in water at pH 6-8 at a temperature of 50-90° C., or reacting ultrasonically, and separating the solid that is crystallized out after reaction;

wherein the stabilizing agent is one or more selected from vitamin C, an ester of vitamin C, a salt of vitamin C, isovitamin C, an ester of isovitamin C, a salt of isovitamin C, dithiothreitol, reductive glutathione or zinc sulfate; and the corresponding salt is a chloride and wherein the high-purity (6S)-5-methyl tetrahydrofolic acid is a composition comprising (6S)-5-methyl tetrahydrofolic acid or a salt thereof, wherein the content of (6S)-5-methyl tetrahydrofolic acid or the salt thereof in the composition is not less than 98.0%, the content of a related impurity JK12A is not greater than 0.1%, and 5-methyl tetrahydropterioic acid is not detectable

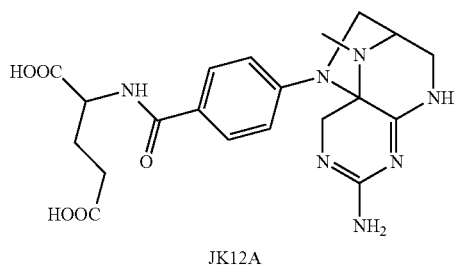 [SMILES: CN1C2CNC3=NC(N)=NCC31N(c1ccc(C(=O)NC(CCC(=O)O)C(=O)O)cc1)C2]

JK12A

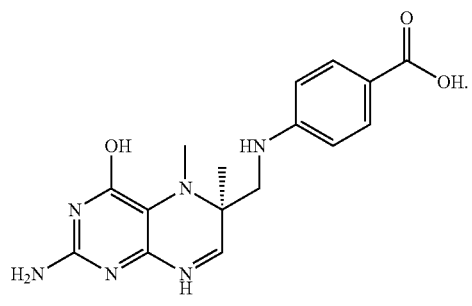

5-methyl tetrahydropterioic acid

5. The method for preparing a solid solution comprising (6S)-5-methyl tetrahydrofolic acid or a salt thereof and a stabilizing agent according to claim 4, wherein during the reaction of the method C, the reaction temperature is 60-80° C., and the pH is 3-4 and adjusted with hydrochloric acid;

and during the reaction of the method D, the reaction temperature is 60-80° C., and the pH is 7-7.5 and adjusted with sodium hydroxide.

6. A pharmaceutical composition, comprising the solid solution according to claim 1.

7. The pharmaceutical composition according to claim 6, which is in the form of common tablets, sustained release tablets, controlled release tablets, effervescent tablets, granules, common capsules, sustained release capsules, controlled release capsules, dry suspensions, oral solutions, oral suspensions, injections, or freeze-dried powder injections.

8. A method of counteracting folic acid antagonists or treating diseases associated with deficiency of 5-methyl tetrahydrofolic acid or a salt thereof in mammals, comprising administering to a patient in need thereof a drug comprising the solid solution according to claim 1, wherein the diseases are selected from the group consisting of subacute encephalitis associated with dementia and vacuolar myelopathy, cerebral folate deficiency, premature obstructive arterial disease, progressive arterial stenosis, intermittent claudication, renal vascular hypertension, ischemic cerebrovascular disease, premature retinal artery and vein occlusion, cerebral occlusive arterial disease, occlusive peripheral arterial disease, magaloblastic anemia due to folate deficiency, and depression.

9. The solid solution according to claim 1, wherein the salt of (6S)-5-methyl tetrahydrofolic acid is a potassium salt, a sodium salt, a calcium salt, a magnesium salt, a barium salt, or a zinc salt.

10. The solid solution according to claim 9, wherein the salt of (6S)-5-methyl tetrahydrofolic acid is a calcium salt.

11. The solid solution according to claim 1, wherein a content of an impurity JK12A is not greater than 0.1%, and 5-methyl tetrahydropterioic acid is not detectable

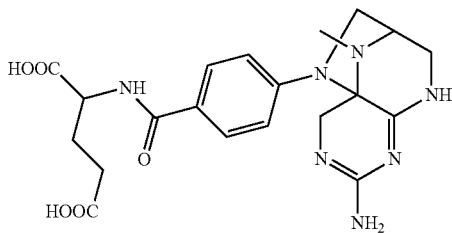

JK12A

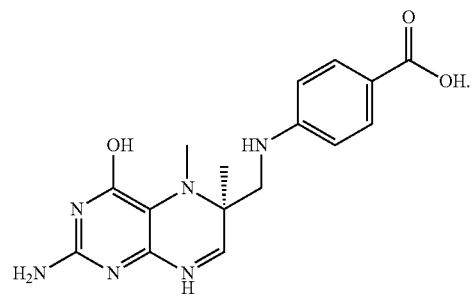

5-methyl tetrahydropterioic acid

12. The solid solution according to claim 2, wherein the total content of the stabilizing agent and (6S)-5-methyl tetrahydrofolic acid or the salt thereof is greater than 99.9%, as determined from the liquid chromatogram of the solid solution.

13. The solid solution according to claim 1, wherein the stabilizing agent is zinc sulfate.

* * * * *